United States Patent [19]
Pinkos et al.

[11] Patent Number: 5,258,555
[45] Date of Patent: Nov. 2, 1993

[54] SYNTHESIS OF CYCLOALKANOLS

[75] Inventors: Rolf Pinkos, Bad Duerkheim; Rolf Fischer, Heidelberg, both of Fed. Rep. of Germany

[73] Assignee: BASF Aktiengesellschaft, Ludwigshafen, Fed. Rep. of Germany

[21] Appl. No.: 956,961

[22] Filed: Oct. 6, 1992

[30] Foreign Application Priority Data

Oct. 25, 1991 [DE] Fed. Rep. of Germany ....... 4135238

[51] Int. Cl.$^5$ .............................................. C07C 35/08
[52] U.S. Cl. .................................... 568/835; 568/832
[58] Field of Search ................ 568/895, 835, 832, 822

[56] References Cited

U.S. PATENT DOCUMENTS

| | | | |
|---|---|---|---|
| 4,507,512 | 3/1985 | Okumura et al. | 568/835 |
| 4,588,846 | 5/1986 | Mitsui et al. | 568/835 |
| 4,661,639 | 4/1987 | Tojo et al. | 568/885 |
| 4,879,422 | 11/1989 | Shirafuji et al. | 568/835 |

FOREIGN PATENT DOCUMENTS

| | | | |
|---|---|---|---|
| 162475 | 11/1986 | European Pat. Off. | 568/835 |
| 3441072 | 11/1987 | Fed. Rep. of Germany | 568/835 |

OTHER PUBLICATIONS

*Chem. Abst.*, vol. 106, No. 20, 1987, p. 108.

*Primary Examiner*—Werren B. Lone
*Attorney, Agent, or Firm*—Keil & Weinkauf

[57] ABSTRACT

A process for the preparation of a cycloalkanol by the reaction of a cycloolefin with water in the presence of a solid acidic catalyst at a temperature of from 50° to 280° C. and under superatmospheric pressure, provided that the temperature and pressure conditions suffice for the formation of a liquid phase comprising water and cycloolefin, wherein a mixture of water and cycloolefin is passed through a fixed bed of solid acidic catalyst with the proviso that no visible liquid phase forms in the bed of solid acidic catalyst.

8 Claims, No Drawings

SYNTHESIS OF CYCLOALKANOLS

The invention relates to a process for the preparation of cycloalkanols by the reaction of cycloolefins with water in the presence of acid catalysts.

DE-PS 3,441,072 describes a process for the preparation of cyclic alcohols, in which cycloolefins are reacted with water in the liquid phase at a temperature of from 50° to 250° C. in hte presence of zeolites having a ratio of acid sites on the shell to the total number of acid sites equal to or greater than 0.07:1 and having a primary particle size of less than 0.5 μm. The reaction is carried out using a suspended zeolite catalyst. This process suffers from the drawback that the powdered catalyst must be separated off after the reaction, which is costly procedure and might cause damage to the catalyst.

Futhermore, EP-A 162,475 discloses that cycloolefins may be advantageously hydrated by using aqueous acids and zeolites containing titanium, zirconium, hafnium, chromium, molybdenum, tungsten, or thorium as building units. This process suffers from the drawback that the aqueous acids must be recovered.

It is thus an object of the invention to provide a process for the preparation of cycloalkanols by the hydration of cycloolefins in which the reaction mixture containing the cycloalkanol is free from catalyst, the catalyst is not damaged and is easy to regenerate, no addition liquid acids requiring recovery are used, and, finally, reactions such as polymer formation or other side reactions are minimized.

This object is achieved by a process for the preparation of a cycloalkanol by the reaction of a cycloolefin with water in the presence of a solid acidic catalyst at a temperature of from 50° to 280° C. and under superatmopheric pressure, provided that the temperature and pressure conditions suffice for the formation of a liquid phase comprising water and cycloolefin, wherein a mixture of water and cycloolefin is passed through a fixed bed of solid acidic catalyst with the proviso that no visible liquid phase forms in the bed of solid acidic catalyst.

One advantage of the novel process is that the reaction mixture is separate from the catalyst. Another advantage of the novel process is that the catalyst is easy to regenerate and no additional liquid acids requiring recovery are used. Yet another advantage of the novel process is the fact that side reactions are minimized.

Preferred cycloolefins have from 5 to 8 carbon atoms in the ring and one olefinic double bond. Examples of suitable cycloolefins are cyclopentene, cyclohexene, and cyclooctene. Cyclohexene is a particularly significant starting material. Alternatively, use may be made of mixtures of cyclohexene, cyclohexane, and benzene, such as are obtained in the partial hydrogenation of benzene, from which cyclohexene may be separated by hydration with the formation of cyclohexanol.

The cycloolefin is reacted with water. Advantageously, from 0.04 to 100 moles of water are used per mole of cycloolefin. Particularly good results are achieved by using from 0.1 to 50 moles of water and more preferably from 0.5 to 10 moles of water, per mole of cycloolefin.

The reaction is carried out at a temperature of from 50° to 280° C. and preferably from 70° to 230° C. and more preferably from 90° to 180° C. In addition, superatmospheric pressure is applied during the reaction. Usually, the pressure used is from 1 to 250 bar and preferably from 2 to 150 bar and more preferably from 4 to 80 bar. The temperature and pressure conditions are matched so as to ensure that a liquid phase comprising water and cycloolefin is formed.

The reaction is carried out in the presence of a solid acidic catalyst. Examples of suitable solid acidic catalysts are strongly acidic ion exchangers such as crosslinked polystyrene containing sulfonic acid groups. Another group of solid acidic catalysts comprises acidic, virtually water-insoluble oxides such as $ZrO_2$, $SnO_2$, $TiO_2$, which may optionally be doped with additional acid groups such as $SO_4^{2-}$. Preferred catalysts are zeolites. Of these, H-type zeolites are preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

It is particularly advantageous to use zeolites of pentasil structure such as zeolite ZSM-5, ZSM-11, and ZBM-10. All of these have as primary structural unit a five-membered ring composed of $SiO_2$-tetrahedra, have a high ratio of silicon dioxide to aluminum oxide, and possess pore sizes which lie between those of zeolite A and those of zeolites X and Y. Good results are achieved when the ratio of silica to alumina in the alumina zeolites is less than 100:1, advantageously between 30:1 and 50:1 and between 70:1 and 90:1 and preferably between 70:1 and 90:1.

The catalysts are generally used in the form of extrudates, spheres, or a powder. Since a dense bed having a large surface area is preferred, a catalyst in pulverized form is particularly suitable, especially when the particle size is from 0.1 to 1 μm. The solid acidic catalysts are used in a fixed bed, for example a cylindrical bed. The solid acidic catalyst, e.g. in powder form, is either packed dry into a tubular reaction zone or is poured in in the form of a suspension in water or the cycloolefin. A frit or some other suitable filter holds the catalyst in position.

The water and cycloolefin, in liquid form, are caused to pass through the fixed bed of solid acidic catalyst, preferably downwardly. It is not necessary to form an intimate mixture of these two components. The application of pressure forces the water and cycloolefin through the fixed catalyst bed, obligatorily in such a manner that no visible liquid phase forms in the catalyst bed. This is achieved by forcing the water and cycloolefin mixture only at such a rate that it can be completely absorbed by the catalyst particles. At the bottom of the catalyst bed there appears an aqueous phase containing a small concentration, e.g., up to 2% w/w, of cycloalkanol and an organic phase, which essentially consists of unconverted cycloolefin plus cycloalkanol.

Usually, the rate of flow of the mixture of water and cycloolefin is from 0.01 to 10 parts by weight per part by weight of solid acidic catalyst per hour. Particularly good results are achieved when from 0.1 to 5 parts by weight of the mixture of water and cycloolefin are passed through the solid acidic catalyst per part by weight thereof per hour.

In a continuous operation, the aqueous phase, replenished with water, is recycled to the top of the catalyst bed, and the organic phase is distilled to remove cycloolefin therefrom, which, after replenishment, is also recycled to the top of the catalyst bed. In this way, the cycloalkanol is removed from the circuit.

When the catalyst, e.g., the zeolite, becomes deactivated after a certain reaction time, it can be regenerated by a simple method, which generally comprises an initial rinse of the fixed bed of solid acidic catalyst with water followed by treatment with an aqueous hydrogen peroxide solution at a temperature of from 50° to 120° C. and preferably from 65° to 80° C. Suitable hydrogen peroxide solutions have a concentration of $H_2O_2$ of from 0.1 to 30% w/w and preferably from 3 to 15% w/w. The state of regeneration is monitored by measuring the pH, which is, for example, 1 to 4 at the commencement of the regenerating operation and rises to 7 during regeneration. Other oxidizing agents may be used in place of hydrogen peroxide for the regeneration, examples of which are ozone, molecular oxygen, air, or peroxo compounds such as peroxosulfates.

The process is illustrated below with reference to the following examples.

EXAMPLE 1

A tubular reactor having a capacity of 50 ml was partly filled with 15.9 g of zeolite ZSM-11 in the form of an aqueous slurry. Per minute, 0.5 g of water and 0.9 g of cyclohexene were passed downwardly through the fixed bed at a bed temperature of 127° C. This was equivalent to 5 parts by weight of water and cyclohexene per part by weight of zeolite per hour. The pressure at the top of the reactor rose to 15 bar.

After a reaction time of 4 h, the concentration of cyclohexanol in the organic phase in the effluent was 9% w/w, and after 8 h it was 11% w/w. Thereafter, the conversion decreased continuously until the said concentration was only 5% w/w after 34 h. The aqueous phase contained from 1 to 2% w/w of cyclohexanol. The zeolite was regenerated by purging the reactor for 12 hours with water at 70°-80° C. and then passing a 5% strength aqueous $H_2O_2$ solution through the reactor at the rate of 1.5 ml/min. The aqueous effluent had a dark color and a pH of 2-3. After 13 h, the effluent was colorless and its pH was 6-7. After heating the reactor to 127° C. and rinsing with water for 5 h, the process was restarted under the aforementioned conditions and achieved the same conversions as before.

EXAMPLE 2

A tubular reactor having a capacity of 150 ml was partly filled with 76 g of zeolite ZSM-5 in the form of an aqueous slurry, and the zeolite was rinsed with 1 ml/min of water for 12 h. A mixture of water and cyclohexene in a molar ratio of 1:2 was then passed through the fixed bed of catalyst at 129° C. and at the rate of 1 part by weight of cyclohexene and water per part by weight of catalyst per hour. The maximum reaction pressure was 35 bar. Cyclohexanol was formed to a maximum concentration in the organic phase of 10% w/w. The aqueous phase contained approximately 2% w/w of cyclohexanol.

EXAMPLE 3

Example 2 was repeated except that the molar ratio of water to cyclohexene was 1.4:1. At a throughput of 0.8 part by weight of cyclohexene and water per part by weight of catalyst per hour, the concentration of cyclohexanol in the organic phase was 10-11% w/w, and at a throughput of 0.4 part by weight of cyclohexene plus water per part by weight of catalyst per hour, the said concentration was 14% w/w. The aqueous phase contained approximately 2% w/w of cyclohexanol.

EXAMPLE 4

Example 3 was repeated except that the molar ratio of water to cyclohexene was 1:1. At a throughput of 0.7 part by weight of cyclohexene and water per part by weight of catalyst per hour, at 160° C., the concentration of cyclohexanol in the organic phase was 13% w/w. The aqueous phase was recycled and replenished with the required amount of water. The organic phase was separated into cyclohexene and cyclohexanol by fractional distillation. The cyclohexene was also recycled. Distillation of the cyclohexanol gave a purity of 99.9% (GC). The bottoms consisted of a small amount of cyclohexylcyclohexene.

The catalyst showed no signs of deactivation after an on-stream period of 180 h. Recycling of the cyclohexene led to the accumulation of a small concentration of methyl cyclopentene, some of which was already present in the cyclohexene used, whilst the rest was formed during the reaction. The total concentration thereof was, however, less than 0.5%.

EXAMPLE 5

1.5 g of zeolite ZSM-11, 0.01 mole of cyclohexene and 0.04 mole of water (ratio by weight of zeolite to cyclohexene plus water 1:1) were placed in a glass autoclave having a capacity of 25 ml. The autoclave was purged with argon and then heated at 120° C. for 1 hour. The autogenous pressure attained a value of 3-4 bar. The contents of the reactor showed no liquid phase either prior to or during or after the reaction. On completion of the reaction, acetone was added to the contents of the reactor in order to separate the reactants from the catalyst. Gas-chromatographic analysis indicated a yield of 17% molar of cyclohexanol based on cyclohexene used. No by-products were found.

COMPARATIVE EXAMPLE

In a manner analogous to that described in Example 5, 1 g of zeolite ZSM-11, 0.01 mole of cyclohexene and 0.1 mole of water (ratio by weight of zeolite to cyclohexene plus water 1:2.6) were placed in a glass autoclave having a capacity of 25 ml. The reactor was purged with argon and then heated at 120° C. for 2 hours without stirring. The autogenous pressure attained a value of 4-5 bar. The contents of the reactor exhibited two liquid phases prior to, during, and after the reaction, the catalyst being mainly present in the bottom (aqueous) phase. On completion of the reaction, the liquid phases were homogenized with acetone. Gas-chromatographic analysis indicated a yield of only 1% molar of cyclohexanol.

We claim:

1. A process for the preparation of a cycloalkanol comprising passing a liquid mixture of water and cycloolefin through a fixed bed of solid acidic catalyst, with the proviso that no visible liquid phase forms in the bed of solid acidic catalyst, at a temperature of from 50° to 280° C. and under superarmospheric pressure, provided that the temperature and pressure conditions suffice for the formation of a liquid phase comprising water and cycloolefin.

2. A process as claimed in claim 1, wherein from 0.1 to 50 moles of water are used per mole of cycloolefin.

3. A process as claimed in claim 1, wherein from 0.01 to 10 parts by weight of a mixture of water and cycloolefin is used per part by weight of solid acidic catalyst per hour.

4. A process as claimed in claim 1, wherein the temperature is maintained at from 70° to 230° C.

5. A process as claimed in claim 1, wherein the pressure is maintained at from 1 to 250 bar.

6. A process as claimed in claim 1, wherein the solid acidic catalyst used is an H-type zeolite.

7. A process as claimed in claim 1, wherein the fixed bed of solid acidic catalyst, when spent, is regenerated with an aqueous solution of hydrogen peroxide and the state of regeneration is monitored by measuring the pH of the effluent.

8. A process as claimed in claim 1, wherein the cycloolefin used is cyclohexene.

* * * * *